(12) United States Patent
Camilli

(10) Patent No.: US 7,479,159 B2
(45) Date of Patent: Jan. 20, 2009

(54) EXTERNAL SUPPORT FOR RESTORING COMPETENCE TO VENOUS VALVES BY TRACTION OF THEIR INTERCOMMISSURAL WALLS

(75) Inventor: Sante Camilli, Rome (IT)

(73) Assignee: Sango S.A.S. Di Cattani Rita & C., Rome (RM) (IT)

( * ) Notice: Subject to any disclaimer, the term of this patent is extended or adjusted under 35 U.S.C. 154(b) by 0 days.

(21) Appl. No.: 11/052,284

(22) Filed: Feb. 8, 2005

(65) Prior Publication Data
US 2006/0178728 A1   Aug. 10, 2006

(51) Int. Cl.
*A61F 2/06*   (2006.01)
*A61F 2/24*   (2006.01)

(52) U.S. Cl. .................... 623/1.24; 623/2.14; 623/2.18; 623/2.37

(58) Field of Classification Search ....... 623/2.11–2.19, 623/2.36, 2.37, 1.24
See application file for complete search history.

(56) References Cited

U.S. PATENT DOCUMENTS

| | | | | | |
|---|---|---|---|---|---|
| 3,357,432 | A | * | 12/1967 | Sparks | .................. 606/151 |
| 4,042,979 | A | * | 8/1977 | Angell | .................. 623/2.37 |
| 4,489,446 | A | * | 12/1984 | Reed | .................. 623/2.37 |
| 5,147,389 | A | * | 9/1992 | Lane | .................. 623/1.24 |
| 5,476,471 | A | * | 12/1995 | Shifrin et al. | .................. 606/151 |
| 5,545,215 | A | * | 8/1996 | Duran | .................. 623/1.26 |
| 5,609,626 | A | * | 3/1997 | Quijano et al. | .................. 623/1.24 |
| 2005/0203617 | A1 | * | 9/2005 | Forster et al. | .................. 623/2.14 |

FOREIGN PATENT DOCUMENTS

WO    WO 97-40755    * 11/1997
WO    WO 02/076305    * 10/2002

* cited by examiner

*Primary Examiner*—Paul Prebilic
(74) *Attorney, Agent, or Firm*—Young & Thompson

(57) ABSTRACT

External support for restoring valvular competence to veins, to be implanted about a vein, along its length. It includes a posterior and an anterior arcuate frame shell, in an elongated material. The posterior frame shell includes two branches of said elongated material penetratingly shaped for an easy insertion thereof behind the posterior wall of the vein, through two paths prepared by the surgeon. Each frame shell includes a respective traction side including longitudinal rectilinear side traction branch elements. The two frame shells are conformed to be juxtaposed to each other about the vein by longitudinal sides thereof. The traction sides are intended to be engaged to the vein by opposite valve intercoinmissural walls via surgical sutures or hook elements to dilate the intercommissural diameter of the vein by traction, so as to absorb the slackening of an incompetent venous valve by extending its cusps.

1 Claim, 1 Drawing Sheet

EXTERNAL SUPPORT FOR RESTORING COMPETENCE TO VENOUS VALVES BY TRACTION OF THEIR INTERCOMMISSURAL WALLS

DISCLOSURE OF THE INVENTION

Technical Field

This invention relates to a device for restoring competence to venous valves.

BACKGROUND OF THE INVENTION

A device for restoring competence to venous valves is known from International Patent Application No. WO 97/40755 (inventor ZUKOWSKI), published on 6th Nov., 1997, having the title Device for restoring Competence to Venous Valves, which is the closest prior art.

ZUKOWSKI's device is based on the discovery that an external force applied onto a vein, at the level of the coapting surfaces of an incompetent, slackened valve of such vein, flattens the vein with the aim to extend the cusps of the valve laterally, taking up their slackening and bringing them into apposition, restoring the competence of the vein.

So ZUKOWSKI's device features a support for applying a compressive, corrective force to an incompetent vein.

ZUKOWSKI discloses a support having a pair of opposite compression membranes which are identical, and generally rectangular. The membranes may have an elliptic or arcuate configuration, or may be flat with curved ends; they are joined together by an integrally formed, intermediate hinge portion which, when the support has been positioned about a valve, generally extends axially with respect to the vein and is placed to be adjacent to one of the commissures where the cusps of the valve attached to opposite walls of the vein meet; the width of the hinge determines the compressive force applied by the support to the valve. The device is implanted by suturing the free edges of the two rectangular members. The sutures perform the same function as the hinge, and they can regulate the compressive force of the device on the venous walls by their degree of tightening.

Problems are associated with ZUKOWSKI's device.

ZUKOWSKI's device has two compression membranes which are continuous surfaces. Owing to such continuity, to implant it, it is necessary to completely clear the posterior wall of the vein from surrounding tissues, and from all eventual collateral veins. Moreover, for the same reason it is not suitable for curing an incompetent valve located at the confluence of another vein owing to the asymmetry and anatomical variability of the confluence itself.

Moreover, the compression from outside envisaged with ZUKOWSKI's device, actually does not ensure a contemporaneous increase of the intercommissural diameter per se. It is a disadvantage of ZUKOWSKI's device that its compressive action actually is not reliable as regards its corrective action.

In fact, it is not sure that applying antero-posterior compressive forces though reducing the antero-posterior diameter of the vein, forcedly determines an enlargement of the latero-lateral intercommissural diameter of the vein valve, because, really, in vivo: depending on the normally arising contraction of the muscular component of the venous wall during the surgical dissection of the vein from the surrounding tissues; depending on blood pressure inside the vein, and, depending on hormone-, or drug-induced contraction of the muscular component of the venous wall, the vein is not in its final condition, as really turns out to be hypothesised in the spirit of ZUKOWSKI's device, so that a calibration thereof is difficult and probably incorrect.

Moreover, the venous spasm directly consequent to surgical manipulation reduces the diameter of the blood-vessel circumferentially, so that one does not have the best apposition of the two valve cusps and therefore it is not possible to check the valve competence intraoperatively, i.e. during an operation.

OBJECTS, CHARACTERISTICS AND ADVANTAGES OF THE INVENTION

It is the object of this invention to provide a device for restoring competence to venous valves that solves such problems.

Such an object is achieved by a traction-acting external support for restoring valve competence to veins that include venous valves become slackened and so incompetent, to be implanted about a vein along the length of the vein; the vein including a posterior and an anterior wall; which external support is comprised of, in combination: two arcuate frame shells, having longitudinal sides, in an elastically flexible elongated material; said frame shells respectively being a posterior or deep frame shell and an anterior or superficial frame shell; said posterior frame shell being comprised of two branches of said elongated material penetratingly shaped for an easy insertion of said posterior frame shell behind the posterior wall of a vein, through two paths prepared by the surgeon; said two penetratingly shaped branches of said elongated material of said posterior frame shell being a proximal and a distal narrow bend of the elongated material, having apices shaped as eyelets; said proximal and distal narrow bends of said posterior frame shell being centrally in continuity with each other by a large, central bend; said anterior frame shell having the same structure as said posterior frame shell, with a proximal bend with an eyelet; a distal bend with an eyelet, and a central bend, but said proximal and distal bends not having to be shaped penetratingly; said two frame shells being conformed to be juxtaposed to each other about a vein by their longitudinal sides, turning their concavities to each other, to assemble the support defining an ellipse-like tunnel to receive the vein thereinto; said two frame shells being integral to each other, being connected to each other by hinge means by a longitudinal side thereof; the external support having a proximal section formed by proximal branches, a proximal branch of said posterior frame shell which is arcuate with its concavity outwards, and a proximal branch of said anterior frame shell which is arcuate with its convexity outwards, so that the external support, once assembled from said frame shells, has an inclined mouth, which can conform itself to the confluence of two veins; each frame shell including a respective traction side including longitudinal rectilinear side traction branch means; said two frame shells having a respective longitudinal side of their arc-like shape intended to constitute such a traction side; said traction sides being intended to be engaged to the vein by opposite valve intercommissural walls by means of surgical sutures to dilate the intercommissural diameter of the vein by traction, so as to absorb the slackening of an incompetent venous valve by extending its cusps.

The critical differences between the support of this invention and ZUKOWSKI's device are the following ones: (a) the inventive support acts by traction, as opposed to compression; (b) it is a device made as a frame shell, as opposed to continuous membranes; (c) the true working parts of it, in its traction work, are the sutures made by the surgeon, as opposed to ZUKOWSKI's device which only requires sutures to be closed.

It is an advantage of the external support of this invention that it can be inserted after an extremely simple dissection of a posterior or deep passage tunnel. The surgeon only has to prepare two paths, without having to dissect the vein all over the length thereof. It can be inserted by easy-insertion branches of elongated material thereof through such passages. As the dissection is lesser than in ZUKOWSKI's device, the related venous spasm is lesser too. This facilitates the significance of the known 'milking manoeuvre', which is less dependable, or not feasible at all, under spasm.

BRIEF DESCRIPTION OF THE DRAWINGS

This invention will be best understood based on the following detailed disclosure of non-limiting preferred embodiments thereof, given in reference to the enclosed drawings, wherein.

DETAILED DISCLOSURE OF THE INVENTION

Figures 1, 1A, 2:
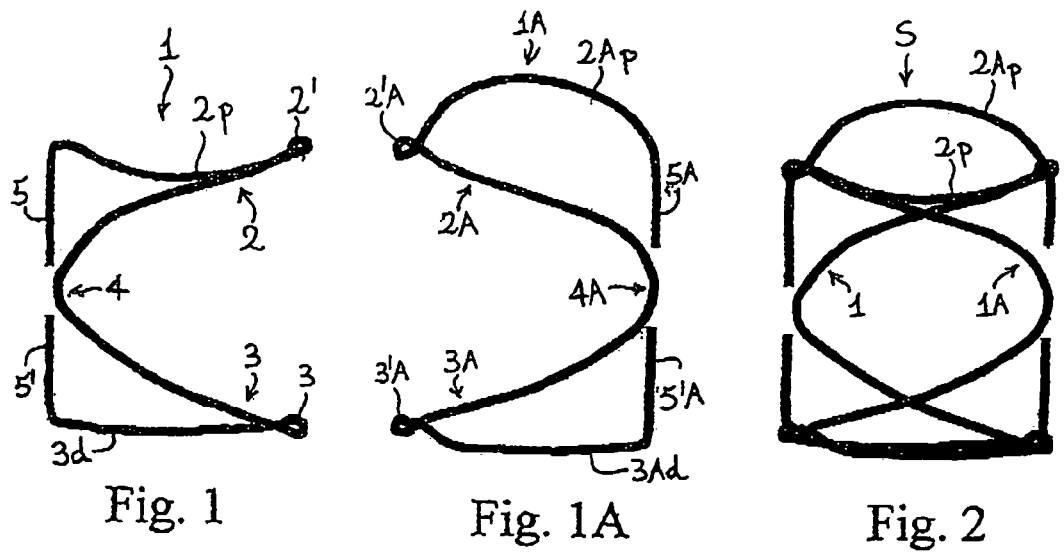
FIG. 1 and FIG. 1A respectively show a posterior and an anterior frame shell of the inventive external support, in a preferred embodiment.
FIG. 2 shows the two frame shells of FIGS. 1 and 1A juxtaposed to each other in an assembled condition, defining an ellipse-like tunnel interior to receive a vein therein, and FIG. 3 schematically shows a vein restored to its competent condition by traction of its valve intercommissural walls by means of the inventive external support, once engaged by the sutures by the same intercommissural walls.

The external support includes two arcuate frame shells in an elongated material, respectively a posterior or deep frame shell 1 (see FIG. 1) and an anterior or superficial frame shell 1A (see FIG. 1A). The external support is intended to be implanted about a vein longitudinally, i.e. along the length of the vein.

The two frame shells are to perform different functions.

Posterior frame shell 1 includes proximal and distal penetratingly shaped branches of the elongated material, for an easy insertion of the posterior frame shell behind the posterior wall of a vein through two paths prepared by the surgeon, without the need for the ligation of eventual collateral veins. The easy insertion branches according to the preferred embodiment depicted in the Figures are proximal and distal narrow bends 2, 3 of the elongated material, having apices shaped as eyelets 2', 3'. Narrow bends 2, 3 are centrally and continuously connected with each other by a large, central bend 4.

Anterior frame shell 1A has the same structure as posterior frame shell 1, with a proximal bend 2A with an eyelet 2'A; a distal bend 3A with an eyelet 3'A and a central bend 4A, but proximal and distal bends do not have to be shaped penetratingly.

The two frame shells have a respective longitudinal side of their arc-like shape intended to constitute a traction side. Such traction sides include respective longitudinal rectilinear side traction branches of the elongated material. According to the preferred embodiment, as depicted in FIGS. 1 and 1A, the traction branches are free-end branches 5, 5' for posterior frame shell 1, and 5A, 5'A for anterior frame shell 1A. The free-end traction branches 5; 5A; 5', 5'A respectively stem as continuations of proximal branches 2p; 2Ap, and of distal branches 3d; 3Ad of proximal 2, 2A and of distal 3, 3A bends of anterior 1 and posterior 1A frame shells, respectively.

Central bends 4, 4A arrive onto the level of the longitudinal traction side of the arc-like shape of the frame shells. The free-end configuration for the traction branches serves to give a degree of elasticity for a better longitudinal flexibility thereof.

Figure 3:
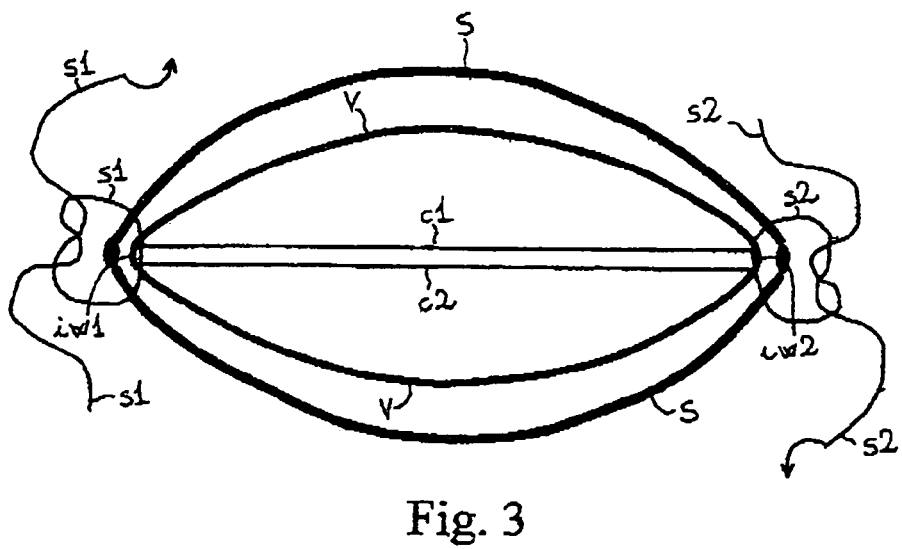

The two frame shells are to be juxtaposed to each other about a vein to be cured by the sides of their arcuate shapes—turning their concavities to each other—to assemble the support as depicted in FIG. 3, defining an ellipse-like tunnel to receive vein V thereinto. The assembled external support S is shown in FIG. 2. In this preferred embodiment, the frame shells are assembled by making free-end traction branches 5, 5' of posterior frame shell 1 to pass into eyelets 2'A, 3'A of anterior frame shell 1A, and making free-end traction branches 5A, 5'A of anterior frame shell 1A through eyelets 2', 3' of posterior frame shell 1. So the eyelets form means for reciprocal reversible mechanical connection of the frame shells.

The external support has a proximal section formed by proximal branches 2p, 2Ap, and a distal section formed by distal branches 3d, 3Ad, and a central section midway therebetween. The front-rear diameter of the support can decrease from the central section to the proximal and the distal section, to emulate the normal anatomic shape of natural valves, which favors the haemodynamic closing of the valves.

Proximal branch 2p of posterior frame shell 1 is arcuate with its concavity outwards, as shown in FIG. 1, whilst proximal branch 2Ap of anterior frame shell 1A is arcuate with its convexity outwards, as shown in FIG. 1A. In this way the external support, once assembled from frame shells 1, 1A as shown in FIG. 2, has an inclined mouth 2p, 2Ap, which can conform itself to the confluence of two veins, at a proximal section thereof.

Referring to FIG. 3, the inventive external support is mounted about a vein V with the longitudinal traction sides of the two frame shells respectively by opposite valve intercommissural walls iw1, iw2. It operates the restoring of the right apposition of the incompetent valve cusps by absorbing their slackening by traction. The traction force is applied onto the intercommissural walls iw1, iw2 of the venous valvular bulb by means of well known surgical sutures s1, s2 and is exerted along the intercommissural diameter—so along valve cusps c1, c2—to dilate it, extending the cusps and absorbing their slackening. Surgical sutures s1, s2 respectively engage traction branches 5, 5'; 5A, 5'A to opposite intercommissural walls iw1, iw2. The surgical sutures can also engage central bends 4, 4A of the frame shells protruding onto the longitudinal traction sides of the frame shells. In FIG. 3 the eccentric ellipse-like shape of vein V, which normally has a circular cross-section, under the action of the inventive support represents the effect of the traction of the latter once engaged by the sutures by the same intercommissural walls.

The frame shells are integral to each other, being connected to each other by a hinge by a longitudinal side thereof.

The elongated material can be metal wire having good flexibility and elasticity, e.g. Nitinol, or medical grade steel such as AISI 316.

However, the elongated material may also be e.g. a biocompatible plastic material, e.g. tetrafluoroethylene such as Teflon®, polypropylene, polyethylene.

This invention has been disclosed referring to specific embodiments thereof, but it is to be understood that variations can be made thereto, without so departing from the scope of protection thereof, which is only restricted by the appended claims.

The invention claimed is:

1. A traction-acting external support for restoring valve competence to veins that include venous valves become slackened and so incompetent, to be implanted about a vein along the length of the vein; the vein including a posterior and an anterior wall; which external support is comprised of, in combination: two arcuate frame shells, having longitudinal sides, in an elastically flexible elongated material; said frame shells respectively being a posterior or deep frame shell and an anterior or superficial frame shell; said posterior frame shell being comprised of two branches of said elongated material penetratingly shaped for an easy insertion of said posterior frame shell behind the posterior wall of a vein, through two paths prepared by the surgeon; said two penetratingly shaped branches of said elongated material of said posterior frame shell being a proximal and a distal narrow bend of the elongated material, having apices shaped as eyelets; said proximal and distal narrow bends of said posterior frame shell being centrally and continuously connected with each other by a large, central bend; said anterior frame shell having the same structure as said posterior frame shell, with a proximal bend with an eyelet; a distal bend with an eyelet, and a central bend, but said proximal and distal bends not having to be shaped penetratingly; said two frame shells being conformed to be juxtaposed to each other about a vein by their longitudinal sides, turning their concavities to each other, to assemble the support defining an ellipse shaped tunnel to receive the vein thereinto; said two frame shells being integral with each other, being connected to each other by hinge by a longitudinal side thereof; the external support having a proximal section formed by proximal branches, a proximal branch of said posterior frame shell which is arcuate with its concavity outwards, and a proximal branch of said anterior frame shell which is arcuate with its convexity outwards, so that the external support, once assembled from said frame shells, has an inclined mouth, which can conform itself to the confluence of two veins; each frame shell including a respective traction side including longitudinal rectilinear side traction branch; said two frame shells having a respective longitudinal side of their ellipse shape adapted to constitute said traction side; said traction sides being adapted to be engaged to the vein by opposite valve intercommissural walls by means of surgical sutures to dilate the intercommissural diameter of the vein by traction, so as to absorb the slackening of an incompetent venous valve by extending its cusps.

* * * * *